United States Patent [19]

Brechot et al.

[11] Patent Number: 6,103,887

[45] Date of Patent: Aug. 15, 2000

[54] NUCLEOTIDE SEQUENCE ENCODING HUMAN CYCLIN A

[75] Inventors: Christian Brechot; Jian Wang; Xavier Chenivesse; Berthold Henglein; Frédérique Zindy, all of Paris Cedex, France

[73] Assignee: Institute National de la Sante et de la Recherche Medicale, Paris, France

[21] Appl. No.: 09/210,889

[22] Filed: Dec. 15, 1998

Related U.S. Application Data

[62] Division of application No. 08/460,895, Jun. 5, 1995, Pat. No. 5,849,508, which is a division of application No. 08/368,403, Jan. 3, 1995, abandoned, which is a continuation of application No. 07/650,805, Feb. 6, 1991, abandoned.

[30] Foreign Application Priority Data

Feb. 12, 1990 [FR] France ..................... 90 01596

[51] Int. Cl.$^7$ ........................ C07H 21/04; C12N 15/11; C12N 15/63
[52] U.S. Cl. ..................... 536/23.5; 536/23.1; 536/24.1; 536/24.2; 435/320.1
[58] Field of Search ..................... 435/7.1, 7.23, 435/7.21, 320.1; 536/23.1, 23.5, 24.1, 24.2

[56] References Cited

U.S. PATENT DOCUMENTS 4,544,545 10/1985 Ryan et al. .

OTHER PUBLICATIONS

Alberts, Bruce et al. Molecular Biology of the Cell, second edition, pp. 95–97, 1989.

Wang, Jian et al. Hepatitis B virus integration in a cyclin A gene in a hepatocellular carcinoma. Nature 343:555–557, 1990.

Xu, Li et al. Factors affecting Long–term Stability of Moloney Murine Leukemia virus–Based Vectors, Virology 171:331–341, 1989.

*Primary Examiner*—Nancy A. Johnson
*Assistant Examiner*—Alana M. Harris
*Attorney, Agent, or Firm*—Larson & Taylor

[57] ABSTRACT

The invention is directed generally to a DNA sequence coding for human cyclin A and in particular to antibodies, or antisera including such antibodies, which bind to human cyclin A as encoded by the sequence of SEQ ID NO: 1 and which are useful in detecting cellular proliferation. The antibodies of the invention can be polyclonal or monoclonal, and are preferably generated by injection of purified human cyclin A into an animal host. The invention is particularly advantageous because it has been discovered that the gene encoding for human cyclin A is a site for integration of the hepatitis B virus associated with hepatocellular carcinoma, and by detecting human cyclin A through the use of the antibodies of the invention, one can detect and diagnose cell proliferation. Through the use of the present invention, cell proliferation and tumorigenesis can thus be detected at early stages, and such conditions can then be treated or inhibited by the use of anti-sense human cyclin A DNA.

5 Claims, 3 Drawing Sheets

AGTAGCTTCTGTACA CATCTCTTGTACA........TGGCGACCACCGT AAAGGAATAATGG

CELLULAR | HBV | CELLULAR

FIG. 2A (194) MRCILVDWLVEVSEEYKLHRETLFLGVNYIDRFLSKISVLRGKLQLVGAA CLAM A
(208) MRAILVDWLVEVGEEYKLQNETLHLAVNYIDRFLSSMVLRGKLQLVGTA HUMAN A
(234) MRSILIDWLVEVSEEYKLDTETLYLSVFYLDRFLSQMAVVRSKLQLVGTA DROSOPHILA A (244) SMFLAAKYEEIYPPDVKEFAYITDDTYTSQQVLRMEHLILKVLTFDVAVP CLAM A
(258) AMLLASKFEEIYPPEVAEFVYITDDTYTKKQVLRMEHLVLKVLTFDLAAP HUMAN A
(284) AMYIAAKYEEIYPPEVGEFVFLTDDSYTKAQVLRMEQVILKILSFDLCTP DROSOPHILA A (294) TTNWF-CEDFLKSCDADDKLKSLTMFLTELTLIDMDAYLKYLPSITAAAA CLAM A
(308) TVNQFLTQYFLHQQPANCKVESLAMFLGELSLIDADPYLKYLPSVIAGAA HUMAN A
(334) TAYVF-INTYAVLCDMPEKLKYMTLYISELSLMEGETYLQYLPSLMSSAS DROSOPHILIA A

FIG.2B (200) MRAILIDWLVQVQMKFRLLQETMYMTVSIIDRFMQNNCVPKKMLQLVGVT HUMAN B
(208) MRAILVDWLVEVGEEYKLQNETLHLAVNYIDRFLSSMSVLRGKLQLVGTA HUMAN A
(198) MRAILIDWLCQVHHRFHLLQETLYLTVAIIDRLLQESPVPRNKLQLVGVT CLAM B (250) AMFIASKYEEMYPPEIGDFAFVTDNTYTKHQIRQMEMKILRALNFGLGRP HUMAN B
(258) AMLLASKFEEIYPPEVAEFVYITDDTYTKKQVLRMEHLVLKVLTFDLAAP HUMAN A
(248) SMLIASKYEEMYAPEVADFVYISDNAYTKKEILEMEQHILKKLNFSFGRP CLAM B (300) LPLHFLRRASKIGEVDVEQ-HTLAKYLMELTMLD-YDMVHFPPSQIAAGA HUMAN B
(308) TVNQFLTQYFLHQQPANCKVESLAMFLGELSLIDADPYLKYLPSVIAGAA HUMAN A
(298) LCLHFLRRDSKAGQVDANK-HTLAKYLMELTITE-YDMVQYLPSKIAAAA CLAM B

NUCLEOTIDE SEQUENCE ENCODING HUMAN CYCLIN A

This is a division of application Ser. No. 08/460,895 filed Jun. 5, 1995, now U.S. Pat. No. 5,849,508, which is a division of application Ser. No. 08/368,403, filed Jan. 3, 1995, now abandoned, which is a continuation of application Ser. No. 07/650,805, filed Feb. 6, 1991, now abandoned.

This invention relates to new compositions containing in a high concentration and/or in a high purity a human cyclin A, said compositions being potentially useful notably for the preparation of detecting agents for cyclin, such as notably antisera or antibodies, whether they be monoclonal or not. The invention also relates to a process allowing one to prepare these compositions.

The invention also relates to a nucleotide sequence coding for human cyclin A as well as expression vectors incorporating this sequence in order to express the cyclin A, and a process for preparing cyclin A and compositions containing cyclin A through expression of these vectors.

The invention also relates to a process and agents for the detection or diagnosis of cell proliferation.

Finally, the invention relates to a process and agents for inhibiting cell proliferation.

It is known that chronic infection with the hepatitis B virus (HBV) is a risk factor for the development of hepatocellular carcinome (22–24) and it has been established that the HBV virus's proviral DNA frequently integrates in the genome of human tumor cells from primary liver cancer (1–4). However, the part played by this integration in liver carcinogenesis is not yet fully understood and evidence of a direct part played by the virus in the cell transformation is scarce. More particularly, the effects of viral DNA integration in the cell genome are open to controversy. The woochuck hepatitis virus (WHV) often appears to act through deregulation of MYC after viral insertion (25). In man, the integration of HBV frequently induces, apparently in a non specific manner, deletions and translocations (3, 26–28). It has however been suggested that the integration on chromosome 11 (3) as well as rearrangement on a locus of chromosome 4q (29, 30) happen in a non random manner. The integration of HBV near a cell gene has been demonstrated only in a tumor in which the viral DNA has interrupted the region encoding for the retinoic acid beta receptor (31, 32).

The invention has allowed one to establish the existence of an individual site for integration of the HBV virus DNA in the human genome (chromosome 4q27) and more precisely in a gene encoding for a human cyclin A whose existence was discovered simultaneously, and that this integration was present in liver cells at an early stage of tumor development without a notable chromosome rearrangement, showing none of the histological characteristics of chronic hepatitis or cirrhosis, in a clonal proliferation of a cell containing only one HBV integration, and was absent in the adjacent liver tissue, so that it is more than likely, through the resulting disturbance of the cyclin A function, that this insertion plays a direct part in liver carcinogenesis.

The inventors have moreover discovered that the expression of cyclin A (mRNA and protein) appeared during step S and step G2/M of the cell cycle and was associated with cell division. Therefore, they found in rat livers during regeneration after partial hepatectomy leading to a synthesis of cell DNA in a high proportion of hepatocytes, a maximum expression of cyclin A (mRNA and protein) during the synthesis step S of the cell DNA.

In the same way, the inventors found that the expression of cyclin A was at a maximum in upper leucocyte myeloblastic acute leucemia with quick doubling time and was very weak in the primitive liver cancer for which the doubling time of the tumor is slow.

The inventors also discovered that it was possible to block the synthesis of cyclin A in hepatocytes with the help of an antidirectional human cyclin A DNA.

According to the invention, the DNA corresponding to the insertion locus was cloned and sequenced and expression vectors allowing the production of a large amount of encoded cyclin A were built, and the object of the invention is thus a process for preparing human cyclin A through genetic expression as well as new compositions with a concentrated human cyclin A content and at a high purity degree.

Object of the invention is also the isolated nucleotide sequence encoding for human cyclin A and vectors containing and/or expressing the sequence encoding for cyclin A.

Object of the invention is notably the sequence designated by N°:1 in the joined list of sequences.

This sequence may be associated with other usual sets such as promoters, initiation or stop signals or introns or other non encoding sequences at the 3' and/or 5' end. It also includes variants notably obtained through substitution of codons or nucleotides preserving the meaning of the code, or through substitutions, insertions or deletions and encoding for an equivalent polypeptide and notably preserving the polypeptide's antigenicity. It also includes any fragment allowing the expression of a polypeptide preserving this antigenicity. Finally, the sequence also includes the human cyclin A gene, possibly incorporating some or all of the elements of an operon, and without natural flanking sequences, and any fragment allowing the expression of a polypeptide preserving an antigenicity of cyclin A.

Object of the invention is moreover a detection process allowing the diagnosis of cell proliferation, in which the level of human cyclin A in the affected cells is determined, notably with the help of polyclonal antibodies, for example, animal antisera which are induced by immunization with human cyclin A or polyclonal antibodies as obtained by expression of the human cyclin A protein in bacterial systems, or monoclonal antibodies antihuman cyclin A.

Object of the invention is thus also these antibodies.

Another object of the invention is a process for treating cell proliferation, in which this proliferation is inhibited with the help of antidirectional human cyclin A cDNA. This cDNA concept also includes the relevant fragments of the cDNA sequence.

In order to ensure its introduction in the cell to be treated, this cDNA may notably be either included in a retroviral vector (for example according to the methods described by J. A. Wolff et al., Proc. Natl. Acad. Sci. 84 : 3344, 1987 or by D. G. Miller et al., Mol. Cell. Biol. 10 : 4239, 1990), or carried by a desialilated protein which may be attached on a receptor which is itself carried by the target cell in view of the penetration of the cDNA in the cell, with the cDNA and protein being notably linked by a polylysin (far exemple according to the methods described by G. Y. Wu & G. H. Wu, J. Biol. Chem. 263 : 14621, 1988 and by G. H. Wu et al., J. Biol. Chem. 264 : 16985, 1989), or included in a liposome.

Object of the invention is thus also the antidirectional cyclin A cDNA, the plasmids including this cDNA and the retroviral vectors which include it.

Object of the invention is also the compound made up by the antidirectional cDNA in the desialilated protein, as well as the liposomes including the antidirectional cDNA.

Other advantages and features of the invention will appear from the following description given as a non-limiting example and referring to the appended drawing wherein:

FIG. 1A represents, the restriction map of the HBV integration area in a tumor cell; the open box represents the 3.1 kb viral insert showing the virus orientation (+); the restriction sites are: B, Bam HI; Bg, Bgl II; E, Eco RI; H, Hind III; P, Pst I; S, Sst I;

sub-clones derived from tumor genome sequences as represented in A, all of them being devoid of repeating sequences; A is a 2.2 kb Sst I/Bgl II fragment; B is a 1.1 kb Eco RI/Bgl II fragment; the X (0.5 kb Bgl II) and Y (0.7 kb Bam HI/Pst I) fragments contain the recombination left and right sites and;

the restriction map of the HBV integration locus in its natural configuration; the arrow shows the viral integration site; the interrupted lines show identical restriction fragments;

FIG. 1C represents, a Northern blot analysis of human new-born liver RNA after hybridization with clone B (line B of FIG. 1); A−: 50 μg poly A− RNA A+: 5 μg poly A+ RNA; sizes are in kb.

FIG. 2 represents:

Figure 1B:
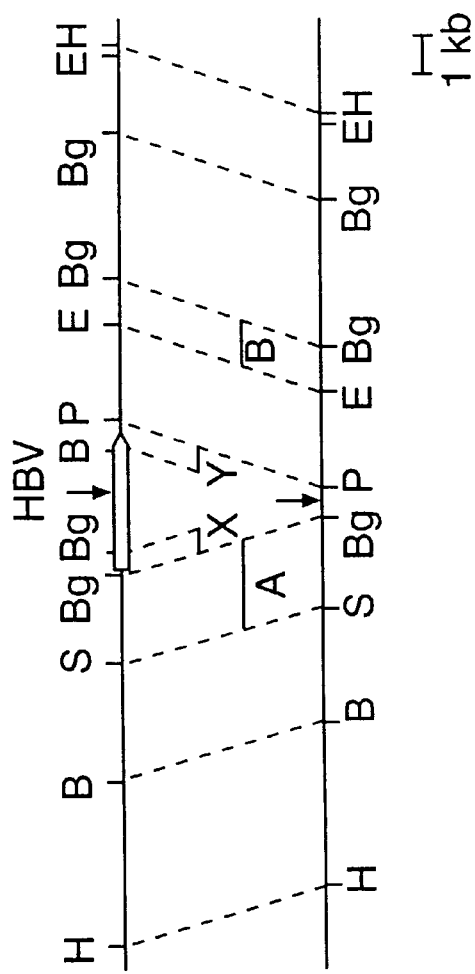
FIG. 1B represents, the virus-host linkage sequence in the locus.

in A, an alignment for comparison of amino acids sequences from S. solidissima (Clam A) (4), D. melanogaster (Drosophile A) (5) and man cyclin A; the identical amino acids are linked with continuous lines and conservative substitutions are linked with an asterisk (*), in B, an alignment of cyclin sequences from S. solidissima (Clam) (15), cyclin B, human cyclin B (12) and human cyclin A.

I. DEMONSTRATION OF THE INSERTION

A well differentiated early primary hepatocellular carcinome (HCC) was analysed as developed in the form of a small nodule, isolated without accompanying cirrhosis in a woman having antibodies against hepatitis B surface antigen. The cell DNA was extracted according to the conventional methods from the tumor tissue on the one hand, and from the non-tumoral adjacent tissue on the other hand. Southern blots of these DNAs were probed with HBV DNA. Whereas in the non tumoral tissue HBV DNA was only present in the form of free molecules, tumoral DNA formed a unique band corresponding to the integration of only one HBV genome copy per cell.

A tumoral DNA phage library was constructed and allowed the isolation of several overlapping clones which were identified with a specific HBV probe. The library was constructed by partial digestion of tumor DNA with Hind III and ligation in Hind III branches of phage L 47. A population of overlapping phage clones was isolated using cloned HBV as a probe. Sub-cloning was made with Bluescript (Stratagene) vectors. The natural allele (FIG. 1c) was cloned from an EMBL 3 library made of placental DNA which was partially digested with Sau 3A I. Sequencing was made by the method described in reference (39).cDNA was isolated from a library constructed from adult human liver mRNA primed with oligo(dT) (32).

The resulting restriction map of the HBV provirus and the flanking cell sequences in the tumor is represented in FIG. 1A. FIG. 1B shows sub-clones A, X, Y, B, without repeating sequences, which were derived from phage clones. The sequencing of fragments X et Y (FIG. 1B) of the provirushost linkage, with detailed restriction analysis of the proviral insert, confirmed that a viral genome without major rearrangements was obtained. The virus-cells linkages were both situated in HBV end zones (nucleotides 1840 and 1617 in the viral core, and open reading frames X, respectively (1) (FIG. 1D)). Hybridation of Southern blots made up from tumor DNA with the A and B probes of FIG. 1B confirmed the genome configuration as represented in FIG. 1A. With probe B, or a 1.1 kb Eco RI/Bgl II fragment, a normal human genome phage library was scanned and several overlapping clones were isolated.

The restriction map of the area wherein HBV integration in its native configuration is made is represented in FIG. 1C. A comparison of restriction maps from FIGS. 1A and 1C shows that viral integration in a tumor did not produce any major rearrangements in its vicinity.

Hybridation of clone B with normal new-born liver polyadenylated and non polyadenylated RNA Northern blots allowed one to identify two 1.8 kb and 2.7 kb transcripted RNA polyadenylated molecules (FIG. 1E). Subsequent screening of a normal human liver cDNA phage library allowed one to isolate five cDNA clones which according to their restriction maps represent the same RNA molecule. The cDNA sequence of the largest (1641 bp) cloned insert is represented in the sequence list (N°.:1) showing an open reading frame (ORF) having a 431 amino acid protein coding capacity and a relative molecular mass Mr=47954. In the reading frame of the conjectured AUG initiation codon is a stop codon in a 30 bp upstream position. The cDNA contains no poly A zone nor any polyadenylation consensus signal.

A comparative research made with the help of a computer has shown that the protein as derived from this insert contains a 150 amino acid region (aa position 209–358) for a cyclin box (9) which is the major preservation area of all known cyclins (4, 5, 7, 9, 12). Comparison for each alignment is represented on FIG. 3, and the protein has a wide similarity with A cyclins from S. solidissima (4) and D. melanogaster (5). In view of the fact that it has only 54 amino acid positions out of 150 which are common to the cyclin spaces of S. solidissima (1) and man (12), B cyclins, the derived protein is a human A cyclin. The N-terminal end of the protein does not show any notable homology with other known proteins, including other cyclins, which is a common feature of known cyclins.

It has turned out that fragment A (FIG. 1B) reacts through hybridization with the cDNA (FIG. 1). Fragments A and B were therefore partially sequenced and sequences were found starting from the 5' and 3' ends of cDNA, respectively. The orientation which is inferred from the cyclin A gene is from left to right on FIG. 1. A study of the sequence then shows that cyclin A has several exons and, because cell sequences of X,Y virus-host linkage fragments (FIG. 1B) are not to be found in the cDNA, it follows that integration of the HBV virus DNA is made in a gene intron.

Viral insertion in the thus discovered locus deregulates operation of the cyclin A gene, which seems to have decisive consequences on the regulation of cell growth. For more details on cyclins A and B, and their importance in mitosis, see 5–21, 33–38.

II. Production of Human A Cyclin Through Genetic Expression.

The cloned cDNA molecule, as represented on the list, is inserted in a bacterial or preferably eukaryotic expression vector, for instance through cloning of the cDNA in the Bluescript cloning vector, insertion in the pET-3b expression plasmid vector, transfection of an host, for instance a bacterial host, the ends of the sequence being determined with the Eco RI and Sma I restriction enzyme. For a detailed description of this method, see: Gene—1987, 56 : 125–135.

A cyclin A preparation may be obtained from the bacterial culture through gel purification.

III. A Study of the Expression of the Cyclin A Gene in Hepatocytes and in Regenerating Liver The cDNA is used as a probe to study the expression of the A cyclin on cultivated hepatocytes and regenerating rat liver models.

Normal rat hepatocytes may be maintained in a primary culture during a period of about 10 days while preserving part of the hepatocyte's differentiated functions. However, there is no cell proliferation. One can stimulate DNA synthesis by adding to the medium some epidermal growth factor, EGF, pyruvate and insulin. A cell DNA synthesis (as mesured by incorporation of tritiated thymidin) is obtained and is at a maximum on the third day of culture. It appeared in Northern blot and Western blot studies that the RNA and cyclin A protein accumulation peaks are to be found during the DNA synthesis step (third day of culture after stimulation), as opposed to the B1 cyclin which is already detected on the first day of hepatocyte culture and is still to be found on the fifth day. Moreover, cyclin A is not detected in hepatocytes whose DNA synthesis was not stimulated (as opposed to cyclin B1).

In order to check that these in vitro observations reflected the true in vivo situation one used a regenerating rat liver model. After a two thirds hepatectomy, a first synchronous mitosis involving about 40% of hepatocytes appears. A cell DNA synthesis between hours twenty and twenty-four is followed about six hours later with the first mitosis. The important point is the more belated starting point of liver non-hepatocyte cell proliferation which will start about twenty-four hours after the proliferation of hepatocytes.

It appeared that:

cyclin A is not detected in a normal liver.

cyclin A is detected (RNA and protein) during the cell DNA synthesis step. Accumulation of cyclin A is followed by a slight decrease in the proportion of cyclin A, then by a new increase during mitosis.

There again, cyclin B1 has a very different profile, being detected in the normal liver, and with its proportion not increasing during step S.

IV. Detection of Cyclin A on Tissue Sections as Obtained by Biopsy.

Starting with frozen sections, a fixation is made with PFA (paraformaldehyde)—PBS 4% during 20 minutes at 4° C. or with methanol during 10 minutes at −20° C., this is washed once with PBS then twice with Tris-HCl (pH 7.6).

Starting with sections included in paraffin, one proceeds to dewax with xylene, the sections are hydrated (from 100% alcohol to distilled water), and are then washed twice with Tris-HCl (pH 7.6).

The rest of the protocol is the following quick immersion in 1% BSA (bovine serum albumin) or Tris-HCl;

incubation with avidin, 15 minutes;

washing with Tris-HCl+immersion in BSA;

incubation with biotin, 15 minutes;

2 washings with Tris-HCl+immersion in BSA;

incubation with normal serum, 20 minutes;

elimination of excess serum;

incubation with a human anticyclin A antibody during one night at 4° C.;

2 washings with Tris-HCl+immersion in BSA;

incubation with a biotinylated revelation antibody, during 30 minutes;

2 washings with Tris-HCl+immersion in BSA;

incubation with the avidin-biotin complex, 30 minutes;

2 washings with Tris-HCl;

revelation with diamino-benzidin (DAB), 5 minutes in the dark;

washings with water;

coloring with hematoxilin;

dehydration in alcohols ( up to 100%);

immersions in xylene:

reading.

Reading allows some quantification of the rate of cyclin A present in the tissue by counting the percentage of labeled cell cores. In the normal liver this percentage is below 1%. Rates reaching 80% have been observed in proliferating tissues.

V. A Process for the Detection or Diagnosis of Cell Proliferation.

As applied to circulating cells, any well known method for detection by antibodies, notably ELISA and particularly ELISA sandwich, as applied to sample taking, may be used.

As applied to tissues, cyclin A is directly detected in tissues as is usually done with known proliferation diagnosis tools.

The preparation of anti-cyclin A antibodies may be made in rabbits by injecting cyclin A as obtained by gel purification in order to obtain a rabbit antiserum.

Detection with quantification of human cyclin A in tissues may then be made by Western blot or immunohistochemistry.

This detection may use a counting of labeled cell cores and a comparison of the rate as counted with the rate of a normal sample of the same tissue.

VI. Inhibition of Cell Proliferation.

In vitro microinjection in hepatocytes, as stimulated by insulin, pyruvate and EGF in a primary culture, of plasmids containing the cyclin A complementary DNA in an anti-directional situation under the control of SV40 virus regulating elements blocks the synthesis of cell DNA.

To ensure the in vivo inhibition of cell proliferation, notably tumoral cell proliferation one uses constructions to bring the anti-directional DNA inside the cell to be treated.

One may first use a retroviral vector (J. A. Wolff et al. & D. G. Miller et al., supra) including the anti-directional cDNA and capable of infecting the target cell and thus to insert the anti-directional cDNA in the genome of this cell. To do so the human cyclin A cDNA is inserted in an anti-directional position into a plasmid, notably the commercial PKC4 plasmid, with an appropriate promotor, for instance the SV40 virus promotor. The plasmids in which the DNA is well integrated in an anti-directional position are then selected with a restriction map before introduction of the cDNA and its promotor into the retrovirus.

One may also use a protein which is capable of binding to a receptor of the target cell. The anti-directional cDNA is then bound to a desialilated protein (G. Y. Wu & C. H. Wu, and C. H. Wu et al., see supra) through a polylysin. After binding to the target cell the cDNA is introduced into the cell cytoplasm wherein it is transcribed into an anti-directional RNA which will block cyclin A synthesis by hybridation on the cell RNA.

One may also use liposomes including the anti-directional cDNA.

REFERENCES

TIOLLAIS, P., POURCEL, C. & DEJEAN, A. Nature 317,489–495 (1985).

BRECHOT, C., POURCEL, C., LOUISE, A., RAIN, B. & TIOLLAIS, P. Nature 286, 533–535 (1980).
NAGAYA, T. et al. Genes and Development 1, 773–782 (1987).
YAGINUMA, K. et al. J.Virol. 61, 1808–1813 (1987).
SWENSON, K. I., FARRELL, K. M. & RUDERMAN, J. V. Cell 47, 861–870 (1986).
LEHNER, C. F. & O'FARRELL, P. Cell 56, 957–968 (1989).
STANDART, N., MINSHULL, J., PINES, J. & HUNT, T. Dev. Biol. 124, 248–258 (1987).
MINSHULL, J., BLOW, J. J. & HUNT, T. Cell. 56, 947–956 (1989).
MEIJER, L. et al. E.MIBO J. 8, 2275–2282 (1989).
PINES, J. & HUNT, T. EMBO J. 6, 2987–2995 (1987).
MURRAY, A. M. & KIRSCHNER, M. W. Nature 339, 275–286 (1989).
PINES, J. & HUNTER, T. Cell 58, 833–846 (1989).
SOLOMON, M., BOOHER, R., KIRSCHNER, M. & BEACH, D. Cell 54, 738–739 (1988).
GOEBL, M. & BYERS, B. Cell 54, 739–740(1988).
WESTENDORF, J. M., SWENSON, K. I. & RUDERMAN, J. V. J.Cell. Biol. 108, 1431–1444 (1989).
DRAETTA, G. et al. Cell 56, 829–838 (1989).
BRIZUELA, L., DRAETTA, G. & BEACH, D. Proc. .Natl. Acad. Sci. U.S.A. 86, 4362–4366 (1989).
DRAETTA, G. & BEACH, D. Cell 54, 17–26 (1989).
LABBE, J. C. et al. EMBO J. 8, 3053–3058 (1989).
MORIA, A. O., DRAETTA, G., BEACH, D., WANG, J. Y. J. Cell 58, 193–203 (1989).
GIORDANO, A. et al. Cell 58, 981–990 (1989).
KEW, M. C. & POPPER, H. Sem. Liver Dis. 2, 136–146 (1984).
BEASLEY, R. P., HWANG L. Y. Sem. Liver Dis. 4, 113–121 (1984).
SAGUMA, K. et al. Hepatology 8, 1642–1646 (1984).
HSU, T. et al. Cell 55, 627–635 (1988).
TOKINO, T. et al. J. Virol. 61, 3848–3854 (1987).
HINO, O., OHTAKE, K. & ROGLER, C. E. J. Virol. 63, 2638–2643 ( 1989).
ROGLER, C. E. et al. Science 230, 319–322 (1985).
PASQUINELLI, C. et al. J. Virol. 62, 629–632 (1988).
BLANQUET, V., GARREAU, F., CHENIVESSE, X., BRECHOT, C. & TURLEAU, C. Human Genetics 80, 274–276(1988).
DEJEAN, A., BOUGUELERET, L., GRZESCHIK, K. H. & TIOLLAIS, P. Nature 322, 70–72 (1986).
DETHE, H., MARCHIO, A., TIOLLAIS, P. & DEJEAN, A. Nature 330, 667–670(1987).
MORGAN, D., KAPLAN, J. M., BISHOP, J. M. & VARMUS, H. E. Cell 57, 775–786 (1989).
SHENOY, S. et al. Cell 57, 763–774 (1989).
McVEY, D. et al. Nature 341, 503–507 (1989).
BUCHKOVICH, K., DUFFY, L. A. & HARLOW, Ed. Cell 58, 1097–1105 (1989).
CHEN, P. L., SCULLY, P., SHEW, J. Y. L. & LEE, W. H. Cell 58, 1193–1198 (1989).
DECAPRIO, J. A. et al. Cell 58, 1085–1095(1989).
SANGER, F., NICKLEN, S. & COULSON, A. R. Proc. Nat. Acad. U.S.A. 74, 5463–5467 (1977).

What is claimed is:

1. An isolated DNA fragment which encodes the human cyclin A and comprises the nucleotide sequence designated SEQ ID NO: 1.

2. The DNA fragment according to claim 1, wherein the nucleotide sequence SEQ ID NO.1 is associated with sets chosen among the group consisting of promoters, initiation signals, stop signals, introns and non encoding sequences at the 3' and/or 5' end.

3. An expression vector comprising an isolated DNA fragment according to claim 1.

4. An expression vector comprising an isolated DNA fragment according to claim 2.

5. The expression vector according to claim 3, wherein it comprises the pET-3b plasmid in which the DNA fragment is inserted.

* * * * *

SEQUENCE LISTING (1) GENERAL INFORMATION:

(iii) NUMBER OF SEQUENCES: 1

(2) INFORMATION FOR SEQ ID NO:1 :

(i) SEQUENCE CHARACTERISTICS:
        (A) LENGTH: 1634 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: HOMO SAPIENS (ix) FEATURE:
        (A) NAME/KEY: Human cyclin A
        (B) LOCATION: coding sequence from base 97 to base 1392,
            coding for a protein of 432 amino acids.

(xi) SEQUENCE DESCRIPTION: SEQ ID NO:1:

```
TATTCTTTGG CCGGGTCGGT GCGAGTGGTC GGCTGGGCAG AGTGCACGCT                    50

GCTTGGCGCC GCACGGTGAT CCCGCCGTCC ACTCCCGGGA GCAGTG                        96

ATG TTG GGC AAC TCT GCG CCG GGG CCT GCG ACC CGC GAG                      135
Met Leu Gly Asn Ser Ala Pro Gly Pro Ala Thr Arg Glu
 1               5                  10

GCG GGC TCG GCG CTG CTA GCA TTG CAG CAG ACG GCG CTC CAA GAG              180
Ala Gly Ser Ala Leu Leu Ala Leu Gln Gln Thr Ala Leu Gln Glu
         15                  20                  25
```

-continued

```
GAC CAG GAG AAT ATC AAC CCG GAA AAG GCA GCG CCC GTC CAA CAA        225
Asp Gln Glu Asn Ile Asn Pro Glu Lys Ala Ala Pro Val Gln Gln
         30              35              40

CCG CGG ACC CGG GCC GCG CTG GCG GTA CTG AAG TCC GGG AAC CCG        270
Pro Arg Thr Arg Ala Ala Leu Ala Val Leu Lys Ser Gly Asn Pro
         45              50              55

CGG GGT CTA GCG CAG CAG CAG AGG CCG AAG ACG AGA CGG GTT GCA        315
Arg Gly Leu Ala Gln Gln Gln Arg Pro Lys Thr Arg Arg Val Ala
         60              65              70

CCC CTT AAG GAT CTT CCT GTA AAT GAT GAG CAT GTC ACC GTT CCT        360
Pro Leu Lys Asp Leu Pro Val Asn Asp Glu His Val Thr Val Pro
         75              80              85

CCT TGG AAA GCA AAC AGT AAA CAG CCT GCG TTC ACC ATT CAT GTG        405
Pro Trp Lys Ala Asn Ser Lys Gln Pro Ala Phe Thr Ile His Val
         90              95             100

GAT GAA GCA GAA AAA GAA GCT CAG AAG AAG CCA GCT GAA TCT CAA        450
Asp Glu Ala Glu Lys Glu Ala Gln Lys Lys Pro Ala Glu Ser Gln
        105             110             115

AAA ATA GAG CGT GAA GAT GCC CTG GCT TTT AAT TCA GCC ATT AGT        495
Lys Ile Glu Arg Glu Asp Ala Leu Ala Phe Asn Ser Ala Ile Ser
        120             125             130

TTA CCT GGA CCC AGA AAA CCA TTG GTC CCT CTT GAT TAT CCA ATG        540
Leu Pro Gly Pro Arg Lys Pro Leu Val Pro Leu Asp Tyr Pro MET
        135             140             145

GAT GGT AGT TTT GAG TCA CCA CAT ACT ATG GAC ATG TCA ATT GTA        585
Asp Gly Ser Phe Glu Ser Pro His Thr MET Asp MET Ser Ile Val
        150             155             160

TTA GAA GAT GAA AAG CCA GTG AGT GTT AAT GAA GTA CCA GAC TAC        630
Leu Glu Asp Glu Lys Pro Val Ser Val Asn Glu Val Pro Asp Tyr
        165             170             175

CAT GAG GAT ATT CAC ACA TAC CTT AGG GAA ATG GAG GTT AAA TGT        675
His Glu Asp Ile His Thr Tyr Leu Arg Glu MET Glu Val Lys Cys
        180             185             190

AAA CCT AAA GTG GGT TAC ATG AAG AAA CAG CCA GAC ATC ACT AAC        720
Lys Pro Lys Val Gly Tyr MET Lys Lys Gln Pro Asp Ile Thr Asn
        195             200             205

AGT ATG AGA GCT ATC CTC GTG GAC TGG TTA GTT GAA GTA GGA GAA        765
Ser MET Arg Ala Ile Leu Val Asp Trp Leu Val Glu Val Gly Glu
        210             215             220

GAA TAT AAA CTA CAG AAT GAG ACC CTG CAT TTG GCT GTG AAC TAC        810
Glu Tyr Lys Leu Gln Asn Glu Thr Leu His Leu Ala Val Asn Tyr
        225             230             235

ATT GAT AGG TTC CTG TCT TCC ATG TCA GTG CTG AGA GGA AAA CTT        855
Ile Asp Arg Phe Leu Ser Ser MET Ser Val Leu Arg Gly Lys Leu
        240             245             250

CAG CTT GTG GGC ACT GCT GCT ATG CTG TTA GCC TCA AAG TTT GAA        900
Gln Leu Val Gly Thr Ala Ala MET Leu Leu Ala Ser Lys Phe Glu
        255             260             265

GAA ATA TAC CCC CCA GAA GTA GCA GAG TTT GTG TAC ATT ACA GAT        945
Glu Ile Tyr Pro Pro Glu Val Ala Glu Phe Val Tyr Ile Thr Asp
        270             275             280

GAT ACC TAC ACC AAG AAA CAA GTT CTG AGA ATG GAG CAT CTA GTT        990
Asp Thr Tyr Thr Lys Lys Gln Val Leu Arg MET Glu His Leu Val
        285             290             295

TTG AAA GTC CTT ACT TTT GAC TTA GCT GCT CCA ACA GTA AAT CAG       1035
Leu Lys Val Leu Thr Phe Asp Leu Ala Ala Pro Thr Val Asn Gln
        300             305             310

TTT CTT ACC CAA TAC TTT CTG CAT CAG CAG CCT GCA AAC TGC AAA       1080
Phe Leu Thr Gln Tyr Phe Leu His Gln Gln Pro Ala Asn Cys Lys
        315             320             325
```

```
GTT GAA AGT TTA GCA ATG TTT TTG GGA GAA TTA AGT TTG ATA GAT        1125
Val Glu Ser Leu Ala MET Phe Leu Gly Glu Leu Ser Leu Ile Asp
    330             335             340

GCT GAC CCA TAC CTC AAG TAT TTG CCA TCA GTT ATT GCT GGA GCT        1170
Ala Asp Pro Tyr Leu Lys Tyr Leu Pro Ser Val Ile Ala Gly Ala
345             350             355

GCC TTT CAT TTA GCA CTC TAC ACA GTC ACG GGA CAA AGC TGG CCT        1215
Ala Phe His Leu Ala Leu Tyr Thr Val Thr Gly Gln Ser Trp Pro
    360             365             370

GAA TCA TTA ATA CGA AAG ACT GGA TAT ACC CTG GAA AGT CTT AAG        1260
Glu Ser Leu Ile Arg Lys Thr Gly Tyr Thr Leu Glu Ser Leu Lys
375             380             385

CCT TGT CTC ATG GAC CTT CAC CAG ACC TAC CTC AAA GCA CCA CAG        1305
Pro Cys Leu MET Asp Leu His Gln Thr Tyr Leu Lys Ala Pro Gln
    390             395             400

CAT GCA CAA CAG TCA ATA AGA GAA AAG TAC AAA AAT TCA AAG TAT        1350
His Ala Gln Gln Ser Ile Arg Glu Lys Tyr Lys Asn Ser Lys Tyr
405             410             415

CAT GGT GTT TCT CTC CTC AAC CCA CCA GAG ACA CTA AAT CTG TAA        1395
His Gly Val Ser Leu Leu Asn Pro Pro Glu Thr Leu Asn Leu
    420             425             430

CAATGAAAGA CTGCCTTTGT TTTCTAAGAT GTAAATCACT CAAAGTATAT             1445

GGTGTACAGT TTTTAACTTA GGTTTTAATT TTACAATCAT TTCTGAATAC             1495

AGAAGTTGTG GCCAAGTACA AATTATGGTA TCTATTACTT TTTAAATGGT             1545

TTTAATTTGT ATATCTTTTG TATATGTATC TGTCTTAGAT ATTTGGCTAA             1595

TTTTAAGTGG TTTTGTTAAA GTATTAATGA TGCCAGCTG                         1634
```